United States Patent [19]

Schneider

[11] Patent Number: 4,495,950

[45] Date of Patent: Jan. 29, 1985

[54] QREEG PROCESS MATRIX SYNCHRONIZER SYSTEM

[76] Inventor: Daniel E. Schneider, 61 E. 93rd St., New York, N.Y. 10028

[21] Appl. No.: 460,094

[22] Filed: Jan. 21, 1983

[51] Int. Cl.³ .............................................. A61B 5/04
[52] U.S. Cl. .................................. 128/670; 128/708; 128/731
[58] Field of Search ................................ 128/670–671, 128/700, 708, 710, 731

[56] References Cited

U.S. PATENT DOCUMENTS

| | | | |
|---|---|---|---|
| 3,706,308 | 12/1972 | John et al. | 128/670 |
| 3,799,147 | 3/1974 | Adolph et al. | 128/700 |
| 4,230,125 | 10/1980 | Schneider | 128/670 |
| 4,422,458 | 12/1983 | Kravath | 128/671 |
| 4,428,380 | 1/1984 | Wong et al. | 128/700 |

FOREIGN PATENT DOCUMENTS 2447052  4/1975  Fed. Rep. of Germany ...... 128/708

OTHER PUBLICATIONS

Paskewitz, "A Hybrid Circuit to Indicate the Presence of Alpha Activity", *Psychophysiology*, vol. 8, No. 1, Jan. 1971.

Klein, "A Waveform Analyzer Applied to Human EEG", *IEEE Trans. Biomed. Eng.*, vol. BME 23, No. 3, May 1976.

*Primary Examiner*—William E. Kamm
*Assistant Examiner*—Mitchell J. Shein
*Attorney, Agent, or Firm*—Felfe & Lynch

[57] ABSTRACT

A QREEG matrix synchronizer system under the aegis of a "master" QREEG tracing has electrodes and sensors for obtaining new computational diagnostic relationships between EEG, EKG, and other life-process data signals from a person's body. A controllable matrix carried by the person's body (into home, field, factory or military operational areas) assembles the data signals on separate channels, one of which carries the "master" combination of the EEG and EKG data signals denominated a QREEG signal. A signal processor makes feasible computing changes in magnitudes and ratios of these signals to detect the loss of or deviation in synchronization between different data signals on the separate channels, and between a data signal obtained at one time and stored for use at a later time and the data signal obtained on the same channel at the later time. These data include those of the waking state and those of the sleep-dream state. All matrix data pertinent to computational diagnostic programs are integrated to forewarn against brain, heart, or other disease if loss or deviation of synchrony occurs. The matrix computation (as well as any isolated tracing or the entire data matrix) is capable of being transmitted from portable instrumentation used in the field to private physicians' offices and/or military and naval bases or to civilian hospitals where confirmation by the accumulated knowledge and expertise in classical EEG-EKG configurations and with reference to data banks may be available.

9 Claims, 9 Drawing Figures

QREEG PROCESS MATRIX SYNCHRONIZER SYSTEM

BACKGROUND OF THE INVENTION

The invention relates to a new diagnostic and computational system for collecting and processing a person's life-process data such as electrocardiogram, electroencephalogram, temperature and respiratory data, during waking states and sleep-dream states and portable for use at home, in the field, factory and among the armed forces of the nation.

In U.S. Pat. No. 4,230,125 issued Oct. 28, 1980 to Daniel E. Schneider, M.D., the inventor also hereof, there is described a method and apparatus for obtaining from a person's body a combined electroencephalogram (EEG) and electrocardiogram (EKG) signal—both integrated into a single continuous tracing—denominated therein a QREEG signal. The QREEG signal is uniquely obtained, moreover, by obtaining the EEG signal component in the usual way from one or more electrodes appropriately positioned on the person's head, but obtaining the EKG signal component with an electrode uniquely in region of the seventh cervical vertebra. In this way, between any two heart QR peaks (the signal-tracing of the heart's left ventricle), there are normally interposed eight alpha waves of lower voltage than the QR's.

In the patent, the QREEG signal components are combined directly for a common display device or a common amplifier for signal processing. The displayed QR signal-tracing of the QREEG is absolutely simultaneous with the QR wave component of the EKG tracing. Between these QR major peaks the eight smaller voltage waveforms of the alpha wave frequency of the EEG signal component, as already noted above. If the displayed QREEG signal tracing were to be superimposed upon any simultaneous EKG tracing, the QR peaks of the two tracings would match precisely, under normal conditions. The patent suggests that it is therefore possible to identify those alpha waves from the QREEG which correspond to those waves of the EKG commonly designated the P and S-T waves.

SUMMARY OF THE INVENTION

The correlation is implemented automatically here, however, without superimposed tracings, by a precise, regular timing ordinate making clear which alpha waves correlate to the P and S-T waves normally during a person's waking state. The more erratic, large, and rapid "spindles" (14–16/sec) associated with a person's Phase I of sleeping and, particularly, the REM waves of the later dream-state (4–6/sec) may also be put into the total synchronous account for the first time in relation to the QR peaks. (REM refers to "rapid eye movements" characteristic of the dream-state.)

In the patent, the QR and alpha wave frequencies in relation to each other and other data are determined and applied to equations in a computer to develop and compare the person's heart and brain weight and body volume to standard values for the person's age. Different categories of deviations from the standard, or pulsing volumes, give forewarning of brain, heart, and other disorders of the person's body.

It remains, therefore, to be disclosed what the new correlations between the QREEG alpha waves and EKG P and S-T waves are and why they are significant when measured by a QREEG matrix synchronizer. Furthermore, if the correlations are to be instantly useful, a way to avoid laboriously comparing tracings visually alone, should be achieved. This is made possible by matricial cross-reference to all the data instantaneously and efficiently integrated in the framework of the precise, regular timer.

The QREEG matrix synchronizer system provides an immediate net print-out indicating the probabilities as to whether danger to health and/or life is present—or not present. The presence of danger would be indicated by a red light properly placed on a keyboard, after computation. A green light similarly placed would indicate no immediate danger.

To these and still further ends, the invention then provides what has been here designated as a "QREEG matrix synchronizer system". The system has electrodes for contacting a person's body—in addition to the "master" QREEG emplacements—in places appropriate for obtaining simultaneous EKG signals, and sensors for sensing the body's variations—waking and sleeping—in temperature and respiration. The electrodes are preferably arranged about the body in accord with the concept that the brain-heart biomagnetic interdynamic is based upon a sphere rather than the old Einthoven triangles alone. In combination with a peripherally and radially controllably interconnectable matrix, the wirings from the electrodes thus positioned according to this concept are denominated herein "circles of circuitry".

The electrodes and sensors are connected individually, or in selected interconnected groups, to the controllable matrix through which the signals from the electrodes and sensors, or groups thereof, can be obtained individually or in combinations as determined by the control of the matrix. This allows immediate or real-time synchronization of the various life-process data (QREEG, EKG, respiration, and temperature) obtained from the electrodes and sensors, invariably and always under the hegemony of the "master" QREEG signal produced as described in the above-referenced prior U.S. Pat. No. 4,230,125 of the same inventor, Daniel E. Schneider, M.D.

In addition to head, shoulders, spine and neck electrodes properly placed the matrix is implemented on a printed circuit board or similar structure which may be worn by the person on the chest and/or back over the heart area. This permits additionally and variously directed "leads". It also provides mobility which is crucial for immediate data gathering from the person at home, in a hospital, at school, in industry, at sports, in military/naval situations, and the other places the person may be.

The QREEG synchronizer matrix also provides convenient versatility, therefore, in obtaining versatile combinations of the signals from the electrodes and sensors for new explorations of, for example, the physiologic and crucial, life-preserving repair and restoration powers of the sleep-dream cycles. This is accomplished through the flexible arrangement and grouping of the electrodes and sensors about the hypothetical sphere of brain-heart biomagnetic interdynamics. The control of the matrix completes the "circles of circuitry" in all possible combinations, and real-time synchronization is thus obtained.

In the system, the matrix "circles of circuitry" connect to a signal processor which, preferably, is also an integrated device of relatively small size to be portably worn by the person. Three processor-embodiments are contemplated. In one, the processor is responsive to the abnormal loss of immediate or real-time synchronization between the QREEG and various segments of the EKG signal components to trigger an alarm reflecting the stress-parameters which might be associated with such loss or deviation from synchronization.

In a second embodiment, the processor includes a memory which stores one or more of the electrode and sensor signals from the circles of circuitry for comparison with the same or another signal at a later time. For example, a "master" QREEG signal compared to EKG signals which are identifiable in the processor as having been obtained while the patient is awake, may also be compared with a "master" QREEG signal in relation to EKG signals identified as from a sleep state. In this way, variable sleep and dream waves may show loss of QR segment synchrony and thus may be used to trigger the alarm.

The preferred form of the memory embodiment also has a sampling device which samples at least the signal for storage over time-separated intervals or "time-slices". Because the life-process data are continuously available, collecting and processing all the data is unwieldly. Sampling the data over discrete "time-slices", for example one, two, or three minutes every hour, therefore provides a way of reducing the continuous data to manageable proportions while retaining all the information of the data over the interval during which it is collected.

The third embodiment of the processor has a modem for connecting the processor to a further processor. The modem, for example, can link a portable processor worn by the person over telephone lines to a more powerful processor at a remote facility, for example a doctor's office or military field or civilian hospital, for further evaluation. Stress upon key or strategically and critically placed personnel may thus be discerned and transmitted to data banks at base.

The three processor embodiments may be combined, of course, to have the features of more than one of the separate embodiments described. Indeed, the full system now contemplated as the best mode has the features of each.

DESCRIPTION OF THE DRAWINGS

A preferred embodiment which is intended to illustrate but not limit the invention will now be described with reference to drawings in which.

(Note 1: All data fed into a graphic continuous recording tracing with computerized "time-slices" and stored on tapes rolled on "floppy" discs.

Note 2: The illustrated matrix of data is aligned on a 60/min or 1/sec heart-rate for purposes of illustration of the synchronizer acting with reference to the QR of the QREEG.)

DESCRIPTION OF THE PREFERRED EMBODIMENTS

Figure 1:
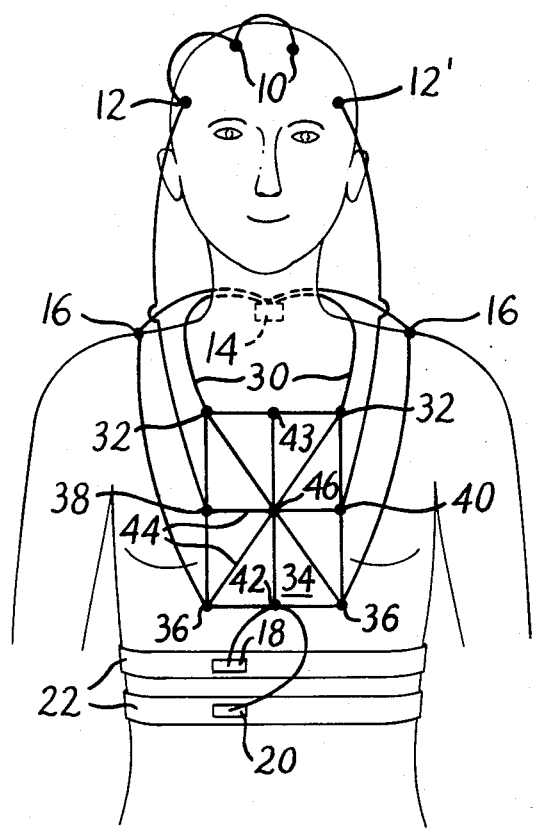
FIG. 1 shows a portion of the preferred embodiment in operative position on a person's body.

FIG. 1 shows electrodes 10, 12, 12', 14 and 16 and sensors 18, 20 which collect life-process data from a person's body B. The electrodes are arranged, roughly, on hypothetical spheres about a person's body in initiation of the concept of circles of circuitry and accord with a spherical concept of brain-heart biomagnetic interdynamics. Electrodes 10, 12, and 12' thus suggest one sphere about a person's head with the electrodes 10 located at the upper portion of the head and the electrodes 12, 12' on the opposite temples. Other head locations are possible and the discrete electrodes 10, 12, 12' may also be replaced by the cap assembly of electrodes and selecting circuitry described in the inventor's beforementioned, prior U.S. Pat. No. 4,230,125. These electrodes 10, 12, 12' sense EEG signals.

Electrode 14 is located over the seventh cervical vertebra on the back of the person's neck. It therefore senses EKG signals as also described in the inventor's beforementioned, prior U.S. Pat. No. 4,230,125. Shoulder or "epaulet" electrodes 16 on the person's opposite shoulders sense augmenting EKG signals. Together, the electrodes 14, 16, are on a rough sphere about the person's chest.

Sensor 18 is a strain gauge or like sensor on a belt 22 about the person's rib cage. It therefore senses the person's respiration through the varying strain in the belt caused by the expansion and contraction of the person's rib cage during respiration.

Sensor 20 is a thermister or like temperature sensor for sensing the person's body temperature. It is held in place by the belt 22. The belt also serves to insulate the sensor from temperature changes on the side away from the body to allow the sensor 20 to sense the person's body temperature more accurately.

A pair of electrically-conducting leads 30 which extend around opposite sides of the person's neck like a necklace connect the electrode 14 to a corresponding pair of uppermost controllable connection nodes 32 of an interconnecting matrix 34. The leads 30 thus also serve to support the matrix 34 on the person's body.

The electrode 14 is also electrically connected to each of the shoulder or epaulet electrodes 16. The shoulder electrodes are, in turn, connected respectively to a lowermost pair of controllable connection nodes 36 of the matrix 34.

The head electrodes 10 are connected to one of the temple electrodes, here electrode 12, and it is connected to a controllable connection node 38 intermediate the upper and lower nodes 32, 36 on one side of the matrix. The other temple electrode 12' is connected directly to a corresponding controllable connection node 40 intermediately on the other side of the matrix.

The respiration and temperature sensors 18, 20 are both connected to a controllable connection node 42 intermediate the lower nodes 36. This electrical connection can be made advantageously along the belt 22 if the belt is physically connected to the lower portion of the matrix to help the necklace leads 30 hold the matrix on the person's body.

A controllable connection node 43 intermediate the nodes 32 on the upper side of the matrix is not used in this embodiment. It could be connected to another electrode. Further, one of the nodes 32 could be connected to still another electrode since the two leads 30 are electrically redundant. Yet other controllable connection nodes could be spaced about the matrix as required for other embodiments having further electrodes and sensors for more or other life-process data.

Figure 2:
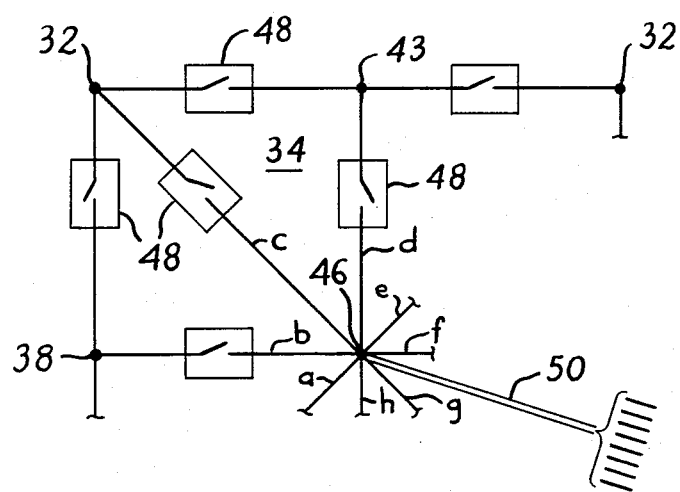
FIG. 2 shows schematically detail of a portion of the embodiment shown in FIG. 1.

FIG. 2 shows schematically a portion of the matrix 34 and some of its controllable connection nodes. The rest of the matrix and nodes are implemented similarly. In the preferred embodiment, the matrix is a printed circuit on a substrate, but in other embodiments it could be discretely wired or an integrated semiconductor. The printed circuit has electrically-conducting elements 44 running peripherially through all the nodes and radially from each node to a central connector 46.

The conducting elements 44 are interrupted between each pair of nodes and between each node and the central connector 46 by a switch 48. The switches 48 thus control the connection of the nodes to the connector and thus the interconnection pattern of the matrix 34. The switches are also illustrated schematically; they may be any suitable manual, electrical, or electronic switching element which may be controllably set to establish the desired matrix interconnections.

A cable 50 having a conductor for each radial connection to a node extends from the central connector of the matrix. The resulting parallel leads or channels from the nodes are labeled a to h.

Figure 3:
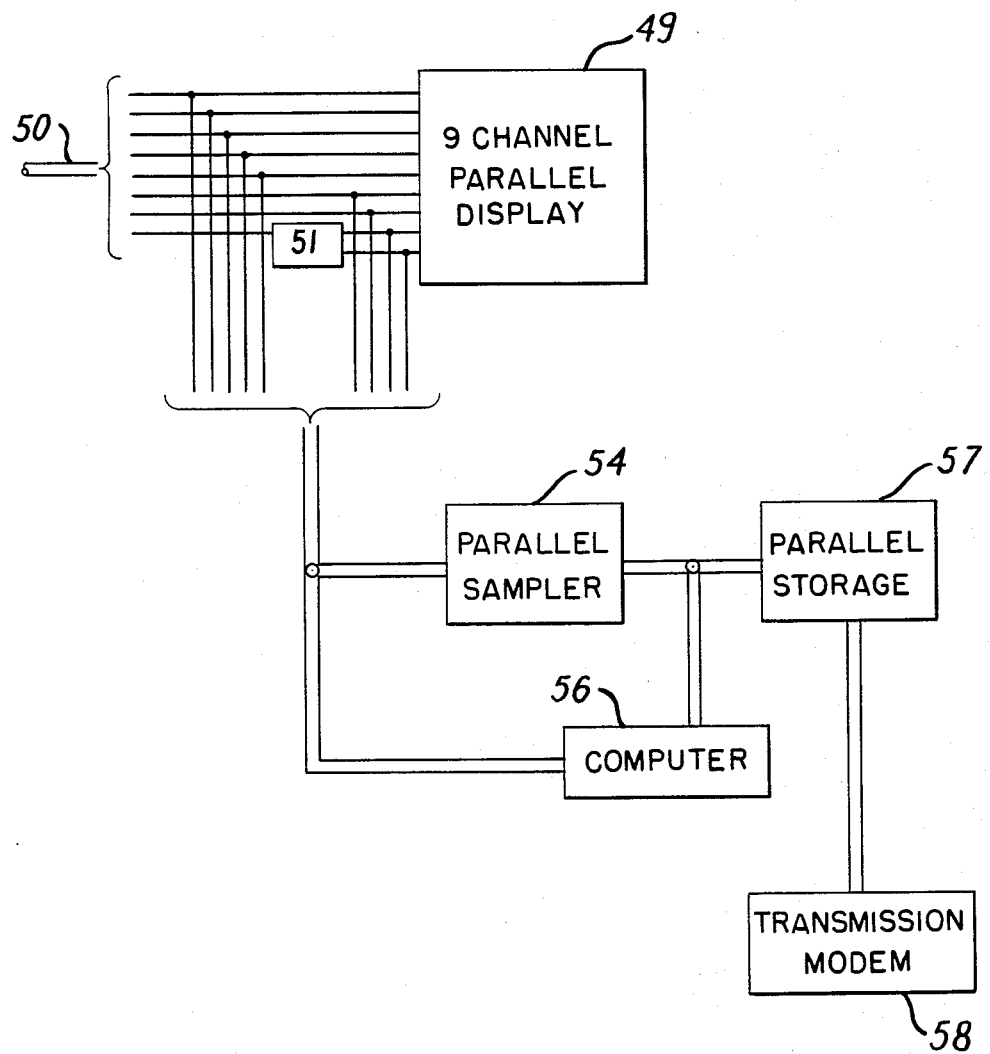
FIG. 3 shows schematically another portion of the preferred embodiment.

In FIG. 3, the eight leads a to h of cable 50 are seen to be connected to a nine channel parallel display 49 such as a nine track pen recorder—and/or stored on tape of a floppy disc—in the preferred signal processor. The ninth channel is derived in a signal discriminator 51 on the lead h from the node 42 (FIG. 1) which is connected to the sensors 18, 20 (FIG. 1). The temperature of the person's body changes much more slowly than the periodic respiration. The signal discriminator can therefore separate the slowly varying temperature signal component from the more rapidly varying respiration signal. For example, if both sensors 18, 20 (FIG. 1) produce a potential signal, the mixed signal will be a respiration oscillation on the relatively constant temperature base potential, and the discriminator 51 could then be a high pass and a low pass filter connected respectively to the separate output channels from the discriminator.

The nine parallel channels are also connected to a further signal processor portion. It comprises a parallel signal sampler 54 and a computer 56. The computer is also connected to the output of sampler 54 so that it may process either the continuous life process data available from the electrodes, the sampled data available from the sampler, or both.

The sampler is a periodically closable switch in each channel lead to sample in parallel the signals in each channel over the interval the switches are closed. The sampler 54 is also connected to a nine channel parallel data storage device 57 such as an appropriately arranged floppy disc. Data stored in the device 57 can be read by the computer 56 or by a transmission modem 58 for transmission to a remote, preferably more powerful computer (not shown) for more detailed analysis. In this way, the computer 56 in the signal processor serves as a basic alarm unit to signal the person to transmit his stored life-process data via the modem to the more powerful computer.

In one preferred use of the system, the appropriate switches 48 are closed to provide on channel b the combined EEG and EKG data from the electrodes 10, 12 and 14 which forms the QREEG signal described in the inventor's beforementioned U.S. Pat. No. 4,230,125.

The switch 48 in channel c is also closed to provide the EKG signal thereon from electrode 14, and the switch 48 in channel h is closed to provide the body temperature and respiration data signal from the sensors 18, 20. This life-process data is fed to the display 49 where they appear as shown in FIGS. 4a, 4b, 4c, and 4e, and to the computer 56. In this use, the computer 56 is programmed as a peak detector for detecting the QR wave peaks of the QREEG and EKG signals, FIGS. 4e and 4c. The QR wave peaks of the QREEG and EKG signals should occur simultaneously as shown. The computer 56 is therefore further programmed for providing an alarm signal if synchronization of the QR waves is lost or suffer deviation.

Figure 4:
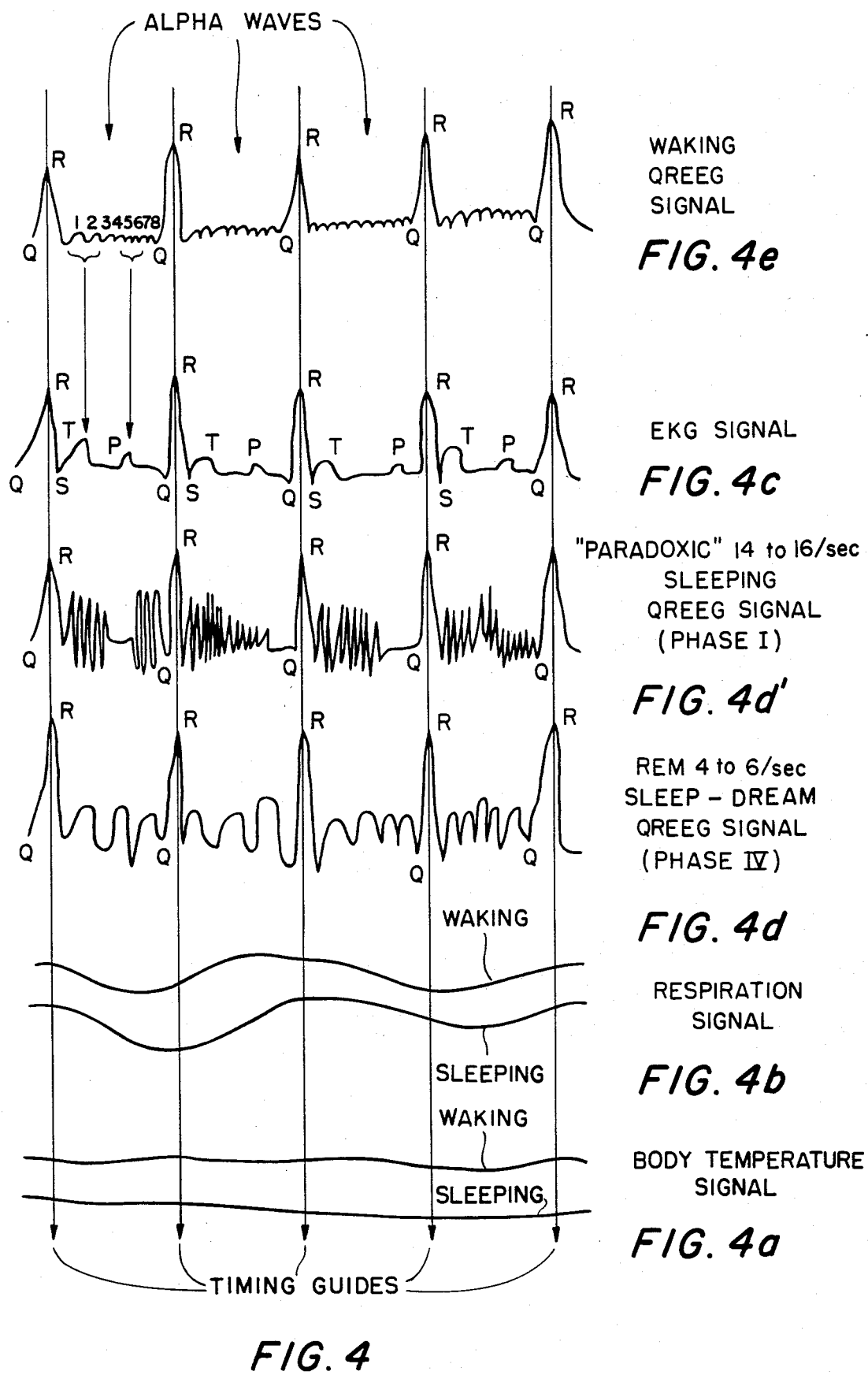
FIGS. 4a to 4e show waveforms which may be displayed on a portion of the embodiment shown in FIG. 3.

In another use, the computer is programmed to distinguish the QREEG signal sleep state patterns (FIG. 4d, 4d') from the waking pattern (FIG. 4e). This can be done from the different period and amplitude of the alpha wave component of the QREEG signals between QR waves. Since the person cannot be simultaneously asleep and awake, the QREEG signal not then being received is selected by the computer from the sampled QREEG signals in the corresponding channel of the storage device 57. The computer then compares, from an initial QR wave peak phase match, the synchronism of successive QR wave peaks in the sleep and waking QREEG signals to again provide an alarm signal upon loss of synchrony of the QR waves.

In still another preferred use, the computer 56 is fed at least QREEG (FIG. 4e) and EKG (FIG. 4c) signals. It is then programmed to detect QR wave peaks in the QREEG signal and to count the alpha waves after each. The interval between the first and second alpha waves in the QREEG signal then corresponds to the normal S-T wave portion of the EKG signal, and the interval between the fifth and sixth alpha waves in the QREEG signal then corresponds to the normal P wave portion of the EKG signal. If relative peaks do not occur in the EKG signal in these intervals, the computer 56 gives an alarm.

Still other uses of the system are contemplated. The computer 56, for example, may be programmed to respond to temperature or respiration deviations from standards for sleep and waking states identified from the QREEG alpha wave patterns (FIGS. 4b and 4e). In some uses, it may be possible to substitute the EEG or EKG signal components of the QREEG signal for the QREEG signal, and such substitution as will be understood by those in the art is specifically contemplated in relation to the claims. The inventor, however, believes that the brain and heart wavefunctions have been artificially separated by the history of their development and that their QREEG unification is the best mode for his invention.

Still other embodiments of the system are also contemplated. For example, at least one of the display devices 49, the collection of the sampler 54, storage device 57, and modem 58, or even the computer 56 can be eliminated. Especially the first may facilitate the portability of the system on the person's body, for example. With respect to the computer 56, it will be appreciated, first, that appropriate programming for the functions described is well within the skill in the art and so dependent on the digital or analog type of computer selected as to require no further description and, second, that it may also be impleted by discrete devices and not by what is normally denominated a computer at all.

The described embodiments and uses, the variations discussed, and such further variations and modifications as may occur to those skilled in the art are intended to be within the scope of the following claims:

What is claimed is:

1. A system, comprising:
   (a) electrode means for obtaining—under the aegis of a "master" QREEG tracing signal—at least EEG and EKG simultaneous and synchronized life-process data signals from a person's body;
   (b) controllable QREEG matrix synchronizer means supported on the person's body for collecting the life-process data signals from the electrode means in separate channels as determined by the control of the matrix, wherein the controllable matrix means comprises means for combining the EEG and EKG signals to provide a QREEG signal on one channel and for providing the EKG signal on another channel; and
   (c) signal processor means for processing the life-process data signals on the separate channels from the controllable matrix means, wherein the signal processor means comprises means operative on the QREEG signal in the one channel for detecting the QR wave peaks of the QREEG signal, means responsive to the detected QR wave peaks for counting the alpha wave in the QREEG signal following each QR wave peak and interposed between any two QR peaks, and means operative on the EKG signal in the other channel for identifying a portion of the EKG signal occurring at a predetermined count of the alpha waves in the QREEG signal.

2. A system as in claim 1, wherein the signal processor means comprises means for detecting loss or deviation of synchrony between the QR wave peaks of the QREEG and EKG signals, particularly the EKG P and S-T waves in relation to the corresponding alpha waves of the QREEG.

3. A system as in claim 1, wherein the signal processor means further comprises:
   (a) means for detecting wave peaks—and their variations or abnormalities—in the EKG signal; and
   (b) means for detecting the absence of synchrony between the P and S-T waves of the EKG signal and the predetermined count of the QREEG's alpha waves.

4. A system as in claim 3, wherein the predetermined count of the QREEG's alpha waves is the interval between the first and second alpha waves (corresponding to the S-T waves of the EKG).

5. A system as in claim 3, wherein the predetermined count of the QREEG's alpha waves is the interval between the fifth and sixth alpha waves (corresponding to the P wave of the EKG).

6. A system as in claim 1, wherein the signal processor means comprises:
   (a) means for storing at least a sample of the QREEG signal provided at one time for use at a later time; and
   (b) means for comparing at least one of the amplitude and frequency of the alpha wave portion of the QREEG signal provided at the later time with that of the stored QREEG signal.

7. A system as in claim 6, wherein the signal processor means further comprises means for periodically sampling the QREEG signal for the means for storing it.

8. A system as in claim 1, wherein the signal processor means comprises:
   (a) means for storing at least a sample of the QREEG signal provided at one time for use at a later time;
   (b) means for detecting the QR waves of the QREEG signal provided at the later time and the stored QREEG signal; and
   (c) means for synchronizing a QR wave of the QREEG signal provided at the later time with a QR wave of the stored QREEG signal and for detecting the absence of synchronism between any following QR waves thereof.

9. A system as in claim 8, wherein the signal processor means further comprises means for periodically sampling the QREEG signal for the means for storing it.

* * * * *